(12) United States Patent
Schneider et al.

(10) Patent No.: US 9,415,182 B2
(45) Date of Patent: Aug. 16, 2016

(54) DISPOSABLE SLEEP AND BREATHING MONITOR

(75) Inventors: Hartmut Schneider, Lutherville, MD (US); Benjamin Richard Lane, Phoenix, MD (US); Alan Richard Schwartz, Baltimore, MD (US); Philip L. Smith, Baltimore, MD (US); Jennifer Anne Regan, Bethesda, MD (US)

(73) Assignees: The Johns Hopkins University, Baltimore, MD (US); Key Technologies, Inc., Baltimore, MD (US)

( * ) Notice: Subject to any disclaimer, the term of this patent is extended or adjusted under 35 U.S.C. 154(b) by 1617 days.

(21) Appl. No.: 11/661,405

(22) PCT Filed: Aug. 26, 2005

(86) PCT No.: PCT/US2005/030328
§ 371 (c)(1),
(2), (4) Date: Feb. 27, 2007

(87) PCT Pub. No.: WO2006/026387
PCT Pub. Date: Mar. 9, 2006

(65) Prior Publication Data
US 2008/0092898 A1   Apr. 24, 2008

Related U.S. Application Data

(60) Provisional application No. 60/605,252, filed on Aug. 27, 2004, provisional application No. 60/652,588, filed on Feb. 14, 2005.

(51) Int. Cl.
*A61M 16/08* (2006.01)
*A61B 5/087* (2006.01)
(Continued)

(52) U.S. Cl.
CPC .......... *A61M 16/0858* (2014.02); *A61B 5/0878* (2013.01); *A61B 5/4806* (2013.01);
(Continued)

(58) Field of Classification Search
CPC . A61M 16/00; A61M 16/0003; A61M 16/06; A61M 16/0816; A61M 16/0841; A61M 16/0858; A61M 16/0875
USPC ............ 128/200.24, 206.28, 206.21, 206.12, 128/204.22, 204.23, 205.25
See application file for complete search history.

(56) References Cited

U.S. PATENT DOCUMENTS 3,395,701 A   8/1968   Bartlett, Jr. et al.
3,675,649 A   7/1972   Basham et al.
(Continued)

FOREIGN PATENT DOCUMENTS

EP         0927538 A2    7/1999
FR         2829942 A1    3/2003
WO    WO 95/06234        3/1995

OTHER PUBLICATIONS

R. E. Oosterbroek et al., "A Micromachined Pressure/Flow-Sensor", Sensors and Actuators, vol. 77 (1999), pp. 167-177.
(Continued)

*Primary Examiner* — Justine Yu
*Assistant Examiner* — Colin W Stuart
(74) *Attorney, Agent, or Firm* — Venable LLP; Henry J. Daley; Laura G. Remus

(57) ABSTRACT

An apparatus comprises a mask, a sensor body configured to be attached to the mask, and an electronic module for producing an output in response to air flow through the sensor body.

26 Claims, 10 Drawing Sheets

(51) Int. Cl.
*A61B 5/00* (2006.01)
*A61M 16/06* (2006.01)
*A61B 5/0476* (2006.01)
*A61B 5/0488* (2006.01)
*A61B 5/0496* (2006.01)
*A61B 5/1455* (2006.01)
*A61M 16/00* (2006.01)

(52) U.S. Cl.
CPC .......... *A61M 16/06* (2013.01); *A61M 16/0683* (2013.01); *A61M 16/0816* (2013.01); *A61B 5/0476* (2013.01); *A61B 5/0488* (2013.01); *A61B 5/0496* (2013.01); *A61B 5/1455* (2013.01); *A61M 16/0051* (2013.01); *A61M 2016/0036* (2013.01); *A61M 2210/0618* (2013.01); *A61M 2230/62* (2013.01)

(56) References Cited

U.S. PATENT DOCUMENTS

| | | |
|---|---|---|
| 3,774,314 A | 11/1973 | Youngs |
| 3,903,876 A | 9/1975 | Harris |
| 3,908,196 A | 9/1975 | Ferraro |
| 4,047,521 A | 9/1977 | Kramer et al. |
| 4,164,942 A | 8/1979 | Beard et al. |
| 4,519,399 A | 5/1985 | Hori |
| 4,957,007 A | 9/1990 | Gray |
| 5,038,773 A | 8/1991 | Norlien et al. |
| 5,088,332 A | 2/1992 | Merilainen et al. |
| 5,197,463 A * | 3/1993 | Jeshuran .................. 128/207.14 |
| 5,265,595 A | 11/1993 | Rudolph |
| 5,379,650 A | 1/1995 | Kofoed et al. |
| 5,505,195 A | 4/1996 | Wolf et al. |
| 5,535,633 A | 7/1996 | Kofoed et al. |
| 5,558,086 A | 9/1996 | Smith et al. |
| D385,960 S | 11/1997 | Rudolph |
| 5,705,735 A | 1/1998 | Acorn |
| 5,750,903 A * | 5/1998 | Ryhanen .................... 73/861.48 |
| 5,789,660 A | 8/1998 | Kofoed et al. |
| 5,857,460 A | 1/1999 | Popitz |
| 6,082,360 A | 7/2000 | Rudolph et al. |
| 6,142,148 A * | 11/2000 | Weckstrom et al. ...... 128/204.22 |
| 6,174,289 B1 | 1/2001 | Binder |
| 6,203,502 B1 | 3/2001 | Hilgendorf et al. |
| 6,224,560 B1 | 5/2001 | Gazula et al. |
| 6,272,905 B1 | 8/2001 | Drzewiecki |
| 6,367,475 B1 | 4/2002 | Kofoed et al. |
| 6,418,929 B1 | 7/2002 | Norfleet |
| 6,435,183 B1 | 8/2002 | Farman |
| 6,470,882 B1 * | 10/2002 | Newhouse et al. ....... 128/200.24 |
| 6,580,944 B1 | 6/2003 | Katz et al. |
| 6,585,662 B1 | 7/2003 | Jones et al. |
| 6,635,021 B1 | 10/2003 | Sullivan et al. |
| 6,718,982 B2 | 4/2004 | Smith et al. |
| 6,726,598 B1 * | 4/2004 | Jarvis et al. ..................... 482/13 |
| 6,742,399 B2 | 6/2004 | Kunz et al. |
| 6,752,766 B2 | 6/2004 | Kowallik et al. |
| 6,758,835 B2 | 7/2004 | Close et al. |
| 6,802,225 B2 | 10/2004 | Shahar et al. |
| 6,959,710 B2 * | 11/2005 | Barnett et al. ............ 128/207.13 |
| 7,004,168 B2 | 2/2006 | Mace et al. |
| 2002/0056452 A1 * | 5/2002 | Brewer et al. ............. 128/202.22 |
| 2002/0116994 A1 * | 8/2002 | Heinonen ....................... 73/196 |
| 2002/0122746 A1 | 9/2002 | Yamamori et al. |
| 2002/0124849 A1 | 9/2002 | Billette De Villemeur et al. |
| 2002/0139368 A1 | 10/2002 | Bachinski |
| 2002/0153012 A1 * | 10/2002 | Gunaratnam et al. ... 128/205.25 |
| 2002/0157672 A1 | 10/2002 | Gunaratnam et al. |
| 2003/0070678 A1 | 4/2003 | Wartman et al. |
| 2004/0094155 A1 * | 5/2004 | Castor et al. ............. 128/204.22 |
| 2004/0102676 A1 | 5/2004 | Brendley |
| 2004/0159323 A1 | 8/2004 | Schmidt et al. |
| 2005/0145247 A1 | 7/2005 | Nashed |
| 2005/0274173 A1 * | 12/2005 | Ebert et al. ...................... 73/37.5 |
| 2006/0021240 A1 * | 2/2006 | Horgan ........................ 33/366.11 |
| 2007/0208269 A1 | 9/2007 | Mumford et al. |

OTHER PUBLICATIONS

European Search Report dated Mar. 23, 2011 for EPO Application 057917767.

* cited by examiner

DISPOSABLE SLEEP AND BREATHING MONITOR

CROSS-REFERENCE TO RELATED APPLICATIONS

This application claims the benefit of International Application No. PCT/US2005/030328, filed Aug. 26, 2005, and U.S. Provisional Patent Application Ser. No. 60/605,252, filed Aug. 27, 2004, and Ser. No. 60/652,588, filed Feb. 14, 2005, which are incorporated herein by reference.

STATEMENT OF GOVERNMENTAL INTEREST

This invention was made with U.S. government support under grant no. HL072126. The U.S. government has certain rights in the invention.

FIELD OF THE INVENTION

This invention relates to air flow monitors and more particularly to air flow monitors for use in monitoring breathing for prolonged time periods.

BACKGROUND OF THE INVENTION

The gold standard for the measurement of respiratory air flow is the pneumotachograph, which determines flow by measuring differential pressure across a fine screen in the flow stream. Pneumotachographs are widely used but limited to 1) short term measurements of ventilation in respiratory medicine and exercise testing, and 2) long term measurements in intubated and unconscious patients who are dependent on a conventional ventilator. The pneumotachograph is rarely used for long term measurements of ventilation in non-intubated, conscious patients and during sleep due to the weight of the pneumotachograph and the discomfort of the pneumotachograph and a mask and headgear that must be worn. However, there is a tremendous need to monitor ventilation in several medical disciplines, particularly during sleep, as sleep unmasks several respiratory disorders, which remain undetected by short term measurements of ventilation during wakefulness.

Sleep induces changes in the respiratory system that affect the central control of either ventilation or upper airway patency. As a consequence, patients may exhibit sleep related breathing disorders that show a clinical spectrum from obstructive sleep apnea to severe hypoventilation in patients with co-morbid cardiopulmonary and neurological disorders. Although the impact of sleep on ventilation is well recognized, quantitative measurement of ventilation has not been well established in clinical diagnostics. This is in part due to the inability to monitor air flow during longer time periods. Instead, less valuable qualitative measures of air flow using a nasal cannula or thermistors are typically performed for diagnosing sleep disordered breathing. Nasal cannulas, nasal prongs, thermistor-based devices, and other qualitative air flow measurement devices are used regularly for overnight sleep studies because they are significantly more comfortable for the patient than pneumotachographs. These semi-quantitative measures of respiration are used to detect apneas and hypopneas by correlating relative changes in the measurement but they are neither suited to quantify the degree of upper airway function (e.g., but not limited to peak inspiratory air flow, inspiratory and expiratory resistance) nor to quantify the level of ventilatory impairment (e.g., but not limited to tidal volume and minute ventilation). Moreover, recent studies demonstrate, that using a quantitative air flow measurement for sleep studies will also improve the detection of mild degrees of sleep related breathing disorders, which remain undetected by the current state of measuring ventilation during sleep. This matter is particularly important in children in which mild degrees of upper airway obstruction (snoring) leads to substantial daytime impairments. Likewise, subtle respiratory disturbances during sleep may trigger adverse cardiovascular events in adults with co-morbid conditions. In summary, the lack of a high quality, quantitative air flow measurement during sleep studies represents a significant loss of valuable clinical information that limits diagnostic accuracy and clinical care. In particular, quantitative flow measurement would allow clinicians to directly measure key respiratory parameters such as breath-by-breath tidal volume, inspiratory flow rates, and timing indices over prolonged periods of time.

Particularly in children, investigators have established that even mild disturbances of breathing during sleep impact academic performance and predict the presence of attention deficit disorders in children. Moreover, early detection of these sleep related breathing disturbances and consequently treatment of these disturbances has been shown to improve these adverse effects.

Currently, no device exists for obtaining a quantitative measurement of respiration during sleep, without disturbing the patient. The pneumotachograph is too cumbersome for use during sleep and the nasal cannula or thermistor only provides a qualitative but not quantitative measure of ventilation.

In summary, particularly in sleep medicine, there is a need for a device that is both comfortable and provides a quantitative, accurate measure of air flow for early detection of sleep related breathing disturbances.

SUMMARY OF THE INVENTION

This invention provides an apparatus comprising a mask, a sensor body configured to be attached to the mask, and an electronic module for producing an output in response to air flow through the sensor body. One version of the apparatus include a light weight headgear for the mask that incorporates electrodes and probes for sensing biomedical signals such as, but not limited to, oxygen saturation, muscle activity (EMG) brain wave activity (EEG) and eye movements (EOG) as well as head position and heart rate.

In another aspect, the invention provides an apparatus comprising a sensor body defining an air passage and configured to be inserted in a breathing tube, wherein the air passing includes a portion having a reduced cross-sectional area, an upstream tube opening and a downstream tube opening positioned in the portion of the air passage having a reduced cross-sectional area, and an electronic module for producing an output representative of air flow in response to differential pressure between pressure at the upstream tube opening and a downstream tube opening the sensor body.

BRIEF DESCRIPTION OF THE DRAWINGS

FIG. 5b is an isometric view of the embodiment of FIG. 5a.

FIG. 5c is a cross-sectional view of the embodiment of FIG. 5a.

DETAILED DESCRIPTION OF THE INVENTION

Figure 1:
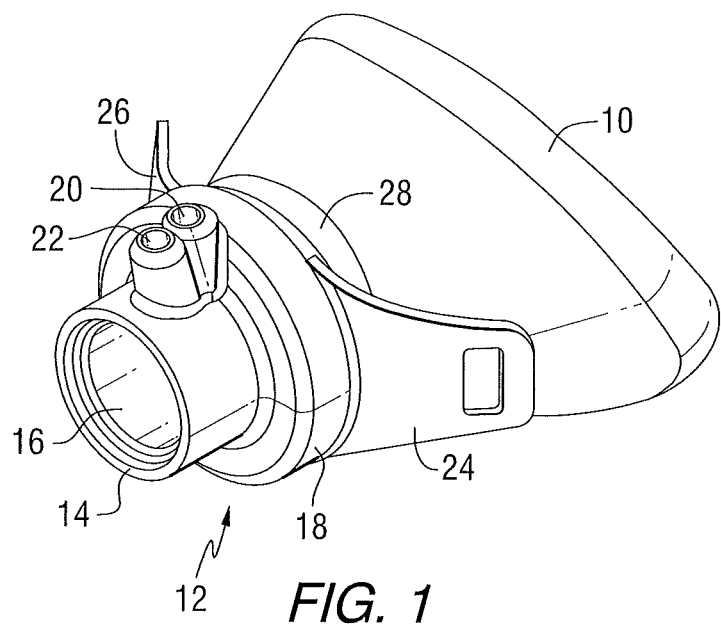
FIG. 1 is an isometric view of a mask and flow sensor module that can be used in the invention.

This invention provides a light weight, low dead-space, disposable breathing sensor and a monitor which can be used for long term measurements of tidal breathing through a nose mask, face mask, tracheostomy or ventilator tubing without adding significant dead space to the airway. In one application, the invention is used for adults and demonstrates that the combined dead space of a small nasal mask and the flow sensor is less than 15 milliliter. Thus, the invention provides an apparatus for measuring air flow quantitatively for prolonged time in non-intubated (Model A in Table 2, and FIGS. 1-4 below) or intubated (Model B in Table 2, and FIG. 5 below) individuals while keeping the added dead space in a range known to be insignificant during sleep. Data from sleep studies in adults show that the breathing monitor is extraordinarily comfortable when worn during sleep and provides an accurate, quantitative measurement of ventilation and respiratory dynamics during sleep.

The light weight of the breathing sensor and flow monitor also obviates the need for wearing a heavy headgear for a tight fit of a mask. Instead, light weighted straps can be used to attach the mask at the nose or face for higher comfort. Two versions of the apparatus have been designed. One version is a flow sensor incorporated in a small nose or face mask attached with only a tiny strap for tightening the mask at the nose or face. A second version provides a light weighted headgear that incorporates electrodes and probes for sensing biomedical signals such as, but not limited to, oxygen saturation, muscle activity (EMG), brain wave activity (EEG), and eye movements (EOG), as well as head position and heart rate. Thus, the invention allows an easy and ready to use measure of tidal ventilation, while measuring sleep parameters, oxygen saturation and body position.

Oxygen saturation is measured by using state of the art pulse oximeters that can be modified to measure oxygen saturation of the forehead or nose. Solid state inclinometers (such as the SQ-SI Series chips provided by SignalQuest, Inc) can be used to sense head position. The sensors can either be integrated into the electronics module attached to the flow sensor or located in a separate electronics module attached to the patient's head remote from the mask. In the latter case, the remote electronics module can communicate with the base unit either via a small wire or wirelessly. A thermistor located on the end of an arm attached to the mask provides a qualitative measure of leakage flow through the mouth. The arm can be snapped to the mask in such a way as to allow for removal of the thermistor assembly in the event that a mouth leakage flow measurement is not desired. The arm can be adjustable to allow the user to position the thermistor directly over the patient's mouth. Electronics to process the thermistor reading will be incorporated into the electronics module for the flow sensor. EEG, EOG, EMG, and heart rate sensors can be incorporated into headgear and electronics.

In addition to the low dead space flow sensor and light weight headgear with or without electrodes and probes, several embodiments are designed to improve handling and comfort for wearing the apparatus and for improving data integrity and artifact elimination. One embodiment of the invention removes the tubes for monitoring the air flow from the sensing part of the apparatus. This embodiment uses an electronics module that is directly attached to the sensing part of the apparatus, and only a thin wire can be connected to the flow monitor in a bedside unit for data output and power. Alternatively, a wireless interface can be provided to transmit the monitored signals to an external unit.

Another feature of the apparatus is that the flow monitoring unit of the apparatus provides quantitative, calibrated measurements of air flow for long term measurement of ventilation. The breathing monitor delivers a stable pre-calibrated air flow signal, which allows for the quantification of ventilation and obviates the need to perform laborious calibration routines prior to each measurement.

Finally, the flow sensing parts of the apparatus can be made of inexpensive plastic parts. Thus the sensor can be applied as a single use, since it is designed as an inexpensive and disposable device for quantitative measurements of ventilation. This is particularly important when measurement of ventilation is warranted in infectious diseases that are known to affect ventilation such as, but not limited to, SARS, pneumonia and TBC.

FIG. 1 is an isometric view of a mask 10 and a disposable sensor body 12 that can be used in monitors constructed in accordance with the invention. The mask can be made of a gas impermeable material that is shaped to fit on the face of a person so as to enclose the nose and mouth of that person (or just the nose in another embodiment). The mask can be flexible to conform to the shape of the face of the person to minimize dead space within the mask. The mask includes an aperture that is generally aligned with the mouth of the person. The disposable sensor body 12 is configured to be connected to the mask to form a substantially airtight seal, and includes a short tubular section 14 that defines an air passage 16. An enlarged rear portion 18 of the sensor body connects to the ring on the mask with a substantially airtight press fit. Openings 20 and 22 are provided to receive tubes that are connected to an electronics module, not shown in this view (or to connect directly to the electronics module in another embodiment with on-board electronics). Strap connectors 24 and 26 extend from the rear portion of the sensor body. One or more straps that extend around a patient's head can be connected to strap connectors. The straps secure the mask to the person's head and also place a force on the sensor body to maintain the press fit between the sensor body and the ring on the mask. A ring 28 on the mask engages a circular groove in the sensor body to form the press fit.

Figure 2:
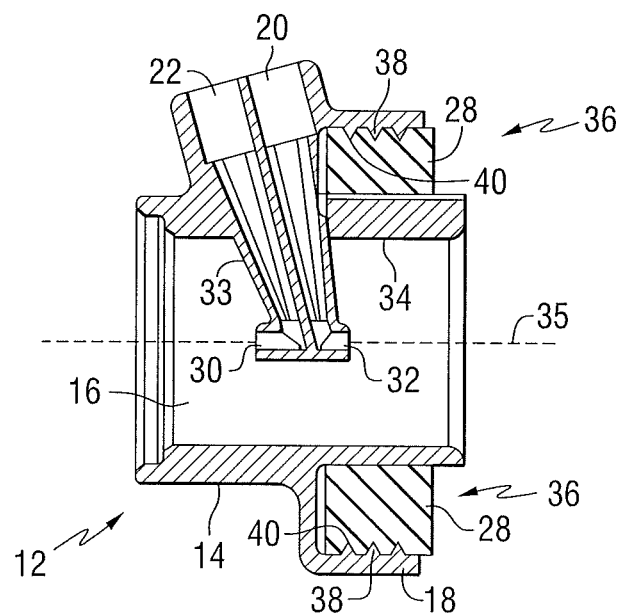
FIG. 2 is a cross-sectional view of the flow sensor module of FIG. 1.

FIG. 2 is a cross-sectional view of the sensor body 12. Two opposing, small diameter tubes 30 and 32 are positioned in a protrusion 33 that extends from the wall 34 of the sensor body into the air passage. The ends of the tubes are located in the center of the air passage to form a measurement section. The end of tube 30 faces the front of the sensor body and the end of tube 32 faces the rear of the sensor body. The tubes penetrate the wall 34 of the sensor body where they mate with flexible tubing that attaches to the electronics module (or connect directly to the electronics module in the embodiment with on-board electronics). The enlarged rear portion of the sensor body is shaped to form an opening 36 that accepts the ring 28 on the mask to form the press fit section for attaching the sensor body to the mask. One or more groove features 38 around the periphery of the ring align with corresponding ribs (also called ridges) 40 in the sensor body to ensure proper alignment of the sensor body in the mask.

An air flow sensor, such as thermistor, can be added to measure leakage through the mouth. A thermistor assembly can include a semicircular ring that snaps onto the mask ring. The snap fit allows for adjustment of the thermistor directly over the mouth of the patient.

The ends of the tubes are positioned substantially along a central axis 41 of the air passage and are spaced from the ends of the sensor body. The tubes penetrate the wall of the sensor body at an angle such that tubes are tilted away from the mask. This allows the sensor body to have a smaller axial length.

The sensor body can be fabricated using a medical grade injection molded plastic (for example, ABS, PVC, or Polycarbonate). The sensor body and flexible tubing can be assembled, sterilized, and packaged as a single, disposable unit. The sensor body can be fabricated with sufficient geometric tolerances such that any differences in the internal geometry of different sensor bodies cannot affect the flow rate measurement.

Figure 3:
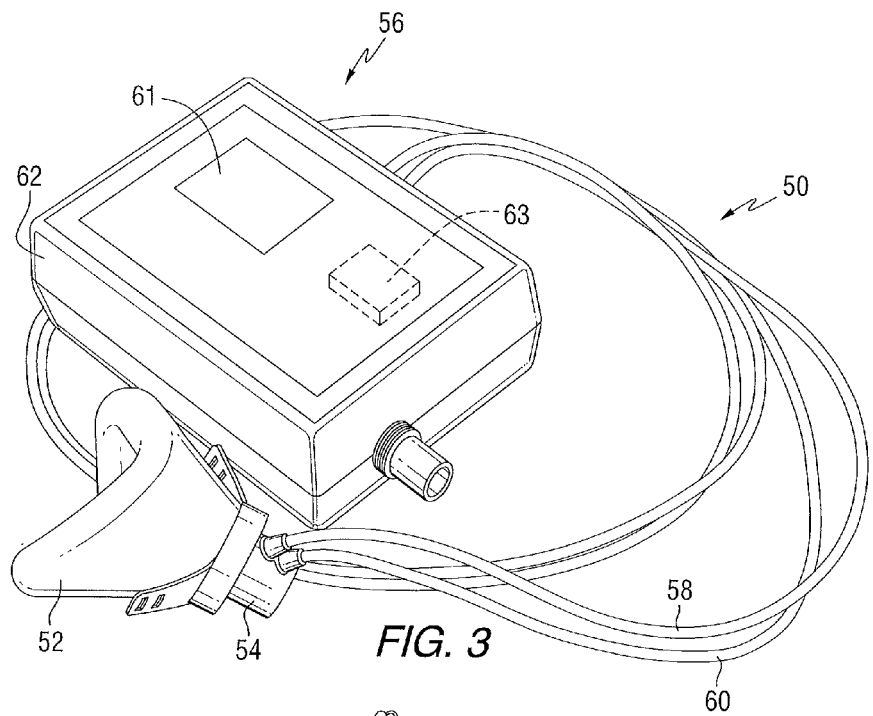
FIG. 3 is an isometric view of another mask and flow sensor module that can be used in the invention.

The mask can be fabricated using a soft durometer material (for example, silicone, latex, or similar materials). FIG. 3 is a pictorial representation of a breathing monitor 50 constructed in accordance with the invention. The monitor includes a mask 52, a sensor body 54 and an electronics module 56. Tubes 58 and 60 are connected between the sensor body and the electronics module. The electronics module includes a molded plastic enclosure 62 containing an electronic circuit board, an interface for the tubing from the sensor body, and an interface for a signal from an oximeter, which can be incorporated into the mask assembly. Standard industrial oximeter probes as they are used in pediatric medicine can be integrated into the mask, and located, for example, at the bridge of the nose or alternatively at the forehead.

Figure 4:
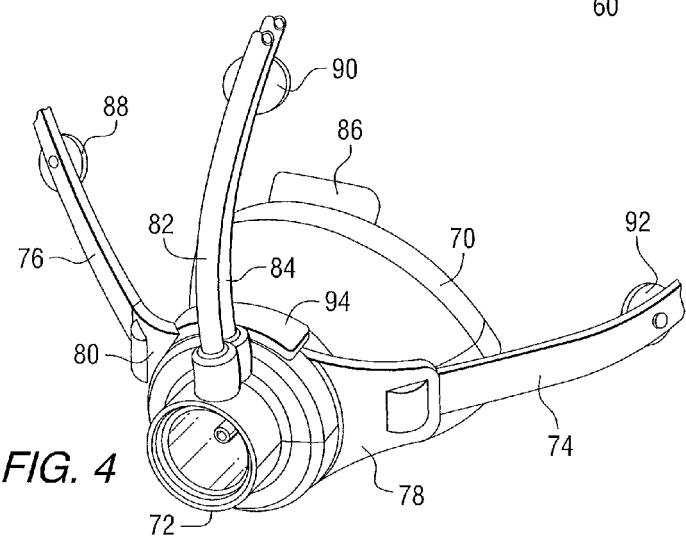
FIG. 4 is a pictorial representation of one embodiment of the invention.

FIG. 4 is an isometric view of another mask 70 and sensor body 72 that can be used in the monitor of this invention. Straps 74 and 76 are shown to be connected to the strap connectors 78 and 80. Tubes 82 and 84 are connected to the sensor body. This embodiment shows an oximeter 86 located near the bridge of the nose portion of the mask or at the forehead. A plurality of sensors 88, 90, 92 and 94 can be incorporated into the device, for example, by being attached to the mask, or the straps, or some other form of headgear. These sensors can provide, for example, biomedical signals such as, but not limited to, oxygen saturation, muscle activity (EMG), brain wave activity (EEG), and eye movements (EOG), as well as head position and heart rate. In one embodiment, sensor 94 can be a motion detector such as an actigraph. Actigraphs are generally used to discriminate between wakefulness and sleep and to determine a sleep-wake pattern.

Figure 5A:
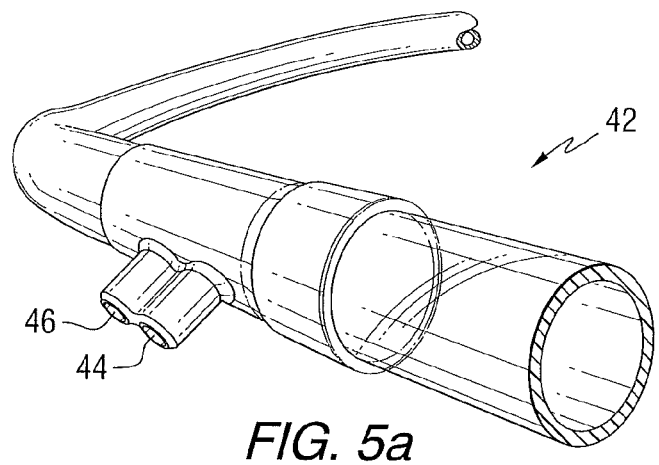
FIG. 5a is a pictorial representation of another embodiment of the invention.

FIG. 5a is a pictorial representation of another embodiment of the invention (hereafter referred to as the "inline meter") that includes a single use disposable sensor body 42 for the wetted portions of a flow tube. The sensor body includes two tubes having upstream and downstream facing ends, similar to those shown in FIG. 2. Tubing is used to connect the sensor tubes 44 and 46 to a monitoring unit that includes a differential pressure transducer.

Figure 5B:
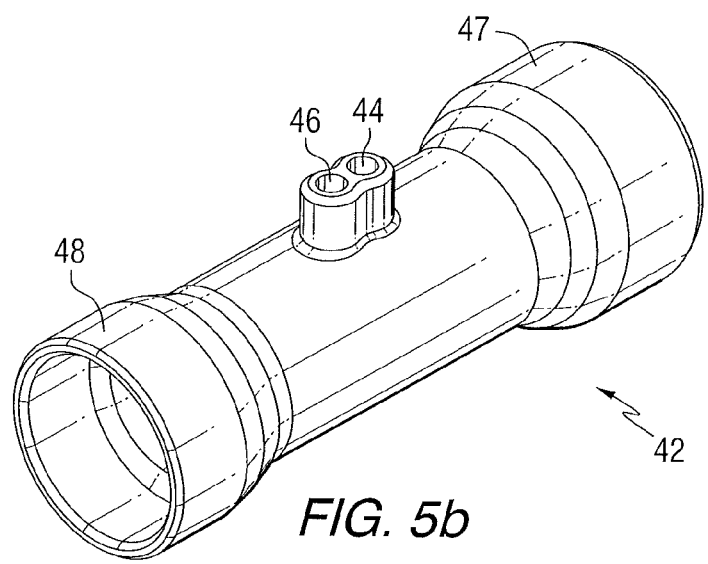
Figure 5C:
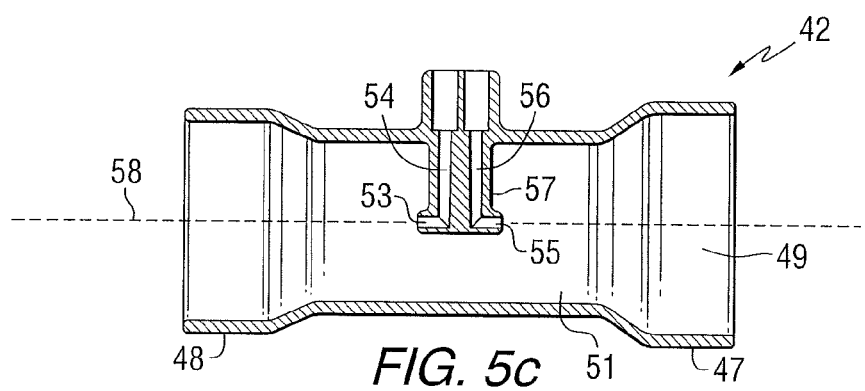

FIG. 5b is an isometric view of the embodiment of FIG. 5a. FIG. 5c is a cross-sectional view of the embodiment of FIG. 5a. The sensor body 42 is shown to include enlarged end portions 47 and 48 that are structured and arranged to couple to a tube containing the air which is to be measured. An air passage 49 is defined by the sensor body. A central portion 51 of the air passage has a reduced cross-sectional area to produce a smoother flow signal with less turbulence induced noise in the measurement section of the sensor. An upstream opening 53 and a downstream opening 55 are positioned at the center of the air passage. The sensor tubes 54 and 56 pass through a protrusion 57 and the sensor body wall.

The inline flowmeter uses the same measurement approach as the mask flowmeter. However, the measurement section of the inline meter has a small flow area, relative to the attached tubing (a feature that is not included in the mask meter because of geometric constraints). The reduced flow area constricts the flow, resulting in a flatter, more uniform velocity profile which produces a smoother flow signal with less turbulence induced noise. Furthermore, the reduced section significantly reduces the impact of upstream flow geometry on the measured flow rate. For instance, upstream bends in the tubing have virtually no impact on the flow measurement, which would not be the case without the reduced section.

In each embodiment, the monitor measures the volume flow rate based on a measured differential pressure, $\Delta P$. The differential pressure is the difference between the pressure in the tube having an end pointing upstream and the pressure in the tube having an end pointing downstream. The volumetric flow rate Q is calculated as $$Q = C\sqrt{\Delta P},$$

where C is a calibration constant that is dependent on the geometry of the sensor body and the density of the fluid being measured.

The electronics module can include a molded plastic enclosure containing an electronics circuit board, a display 61, an external power jack, and a connector for output of the flow rate signal. The circuit board can contain a Micro-Electro-Mechanical system (MEMs) differential pressure sensor 63 and the necessary electronics components for converting the analog voltage equivalent to the differential pressure into either a voltage or current equivalent to the calculated flow rate. The sensor can have sufficiently small linearity error and hysteresis to not affect the flow rate measurement.

Gas flow measurement can be performed using a number of methods. The flow sensor of the invention uses the measure of the difference between total and static pressure to calculate the air velocity and then determines flow rate based on that velocity. This approach is widely used in many industries (the most familiar implementation is the Pitot tube) and is based on the Bernoulli Equation:

$$p + \tfrac{1}{2}\rho V^2 + \rho gh = \text{constant},$$

where: p=pressure; $\rho$=density; V=velocity; g=gravity; and h=elevation.

The equation is a valid ideal measure at any point along a stream line for steady flows with constant density and for which friction is negligible. As shown in FIG. 2, the flow sensor includes two pressure measurement ports located at the centerline of the flow sensor; one pointing upstream and one pointing downstream. Applying Bernoulli's Equation to this configuration, the differential pressure measured between the ports relates to the fluid velocity as:

$$p_{up} - p_{dn} = \tfrac{1}{2}\rho V^2,$$

where $p_{up}$ is the upstream pressure, $p_{dn}$ is the downstream pressure, and V is the velocity at the centerline of the flow sensor.

The flow rate is calculated from the centerline velocity as:

$$Q = CVA$$

where: Q=flow rate; A=cross-sectional area of the flow sensor; and C=correction factor to account for the velocity profile in the flow sensor.

In turbulent flow in a tube, the velocity profile is effectively flat, thus C is very close to 1.0. In fully developed laminar flow in a tube, the velocity profile is parabolic and C is closer to 0.5. Consequently C varies with velocity and must be determined experimentally in all but the most ideal flow conditions. Instrument calibration serves to establish a value for C depending on the 1) embodiment of the invention, 2) the flow rate, and 3) the direction of the air flow. The use of a repeatable manufacturing process for the metering section precludes the need for calibration before each use (as is currently required for existing pneumotachographs).

Data acquired using early flow sensor prototypes are shown below. Collection of the data was covered by IRB protocol 04-05-18-02, entitled, Trans Nasal Insufflation for the Treatment of Snoring and Obstructive Apnea, with continued use through IRB protocol number 05-03-10-01.

Figure 6A:
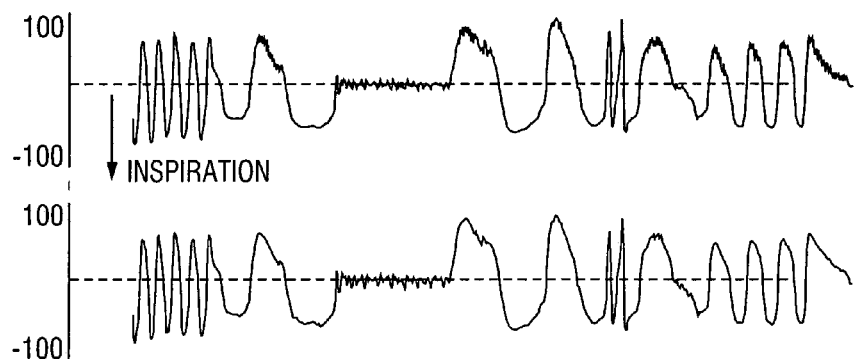
FIG. 6a is a graph of a breathing pattern.
Figure 6B:
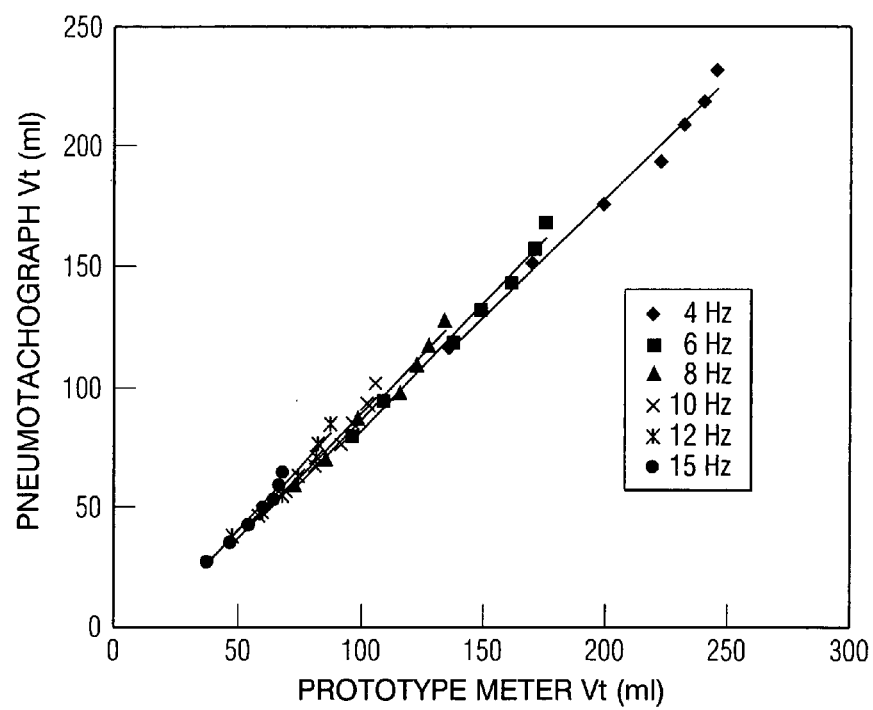
FIG. 6b is a graph showing the performance of one embodiment of the invention.

FIGS. 6a and 6b show the correlation between a prototype of the flow sensor and pneumotachograph measurements of flow rate and tidal volumes (Vt) at frequencies ranging from 4 to 15 Hz. To obtain the data, the flow sensor was placed inline with a pneumotachograph and data from each instrument was sampled simultaneously during flow testing. Flow rate data was acquired for flow patterns typical of breathing (FIG. 6a) and at frequencies ranging from 4 Hz to 15 Hz (FIG. 6b). In FIG. 6a, the top trace was produced using a pneumotachograph, and the bottom trace was produced using a monitor constructed in accordance with this invention. The higher frequency air flows were generated by a high frequency ventilator.

FIGS. 6a and 6b show the correlation between the monitor of this invention and a pneumotachograph. Measured air flow is shown in FIG. 6a. Measured tidal volume at 4-15 Hz is shown in FIG. 6b. The data in FIGS. 6a and 6b show that the flow sensor compares well with the pneumotachograph. In fact, the high frequency data suggest that the prototype can accurately measure ventilation over the entire frequency range with a mean difference of less than 8%. No device available is currently adapted for continuous quantitative monitoring of tidal air flow characteristics.

Figure 7:
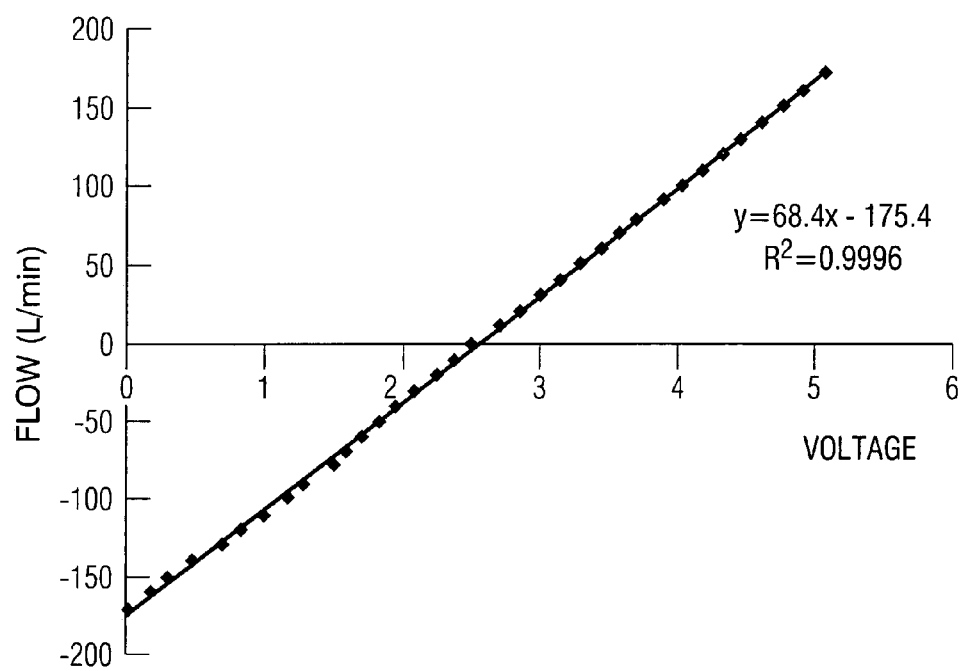
FIG. 7 is a graph of flow versus voltage.

FIG. 7 shows calibration data for the monitor of this invention, using a pneumotachograph as a standard. The voltage output of the monitor of this invention is shown with respect to the flow indication of a serially connected pneumotachograph. The voltage output of the monitor of this invention is linear with output flow. As shown in the FIG. 7, the correlation is very good between the two measurements with insignificant deviation.

One of the key features of an accurate ventilation measurement is flow measurement stability, i.e., lack of drift over a long term measurement. Tidal volume is obtained by integrating a flow measurement, so if an inaccurate flow sensor drifts over time, errors can accrue to unacceptable levels for tidal volume and minute ventilation (the volume of air ventilated in one minute).

Figure 8:
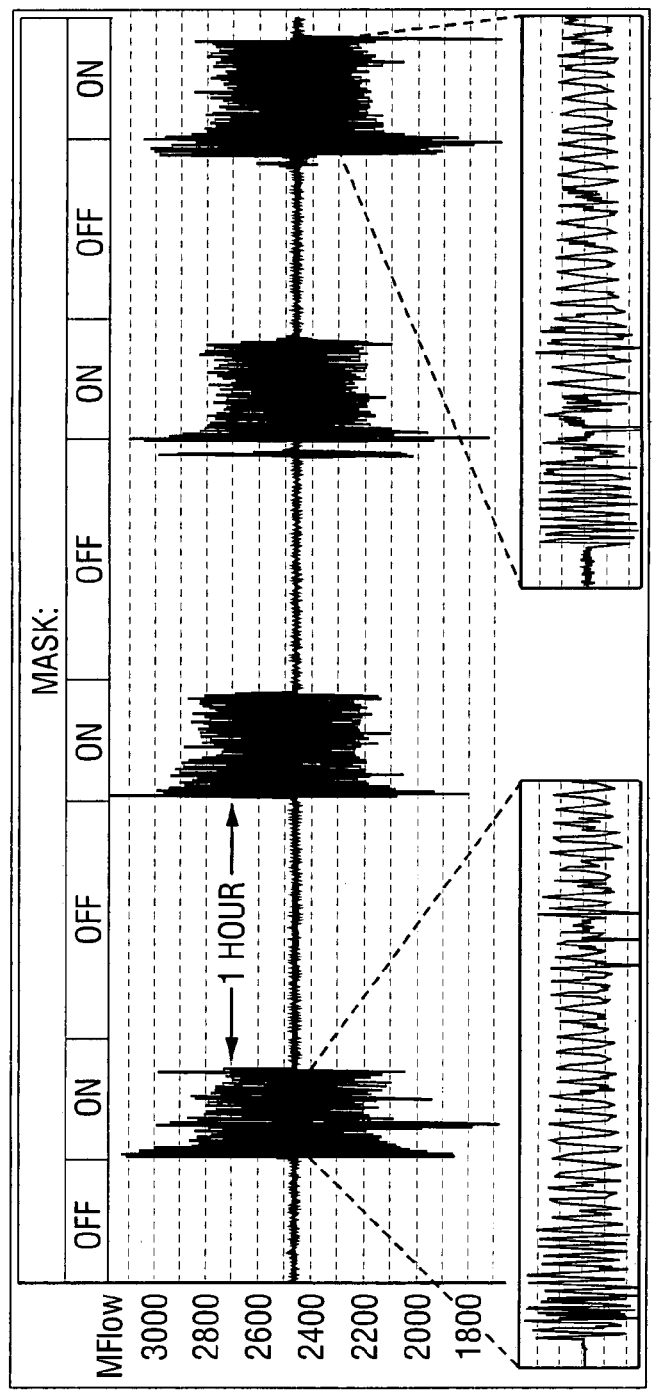
FIG. 8 is a graph showing the stability of one embodiment of the invention.

FIG. 8 shows the stability of a monitor constructed in accordance with this invention over a 7 hour period during on-off use with four sequences of patient breath flow measurement. This FIG. 8 suggests that stability over the longer term (e.g., overnight studies) may be very good.

Figure 9:
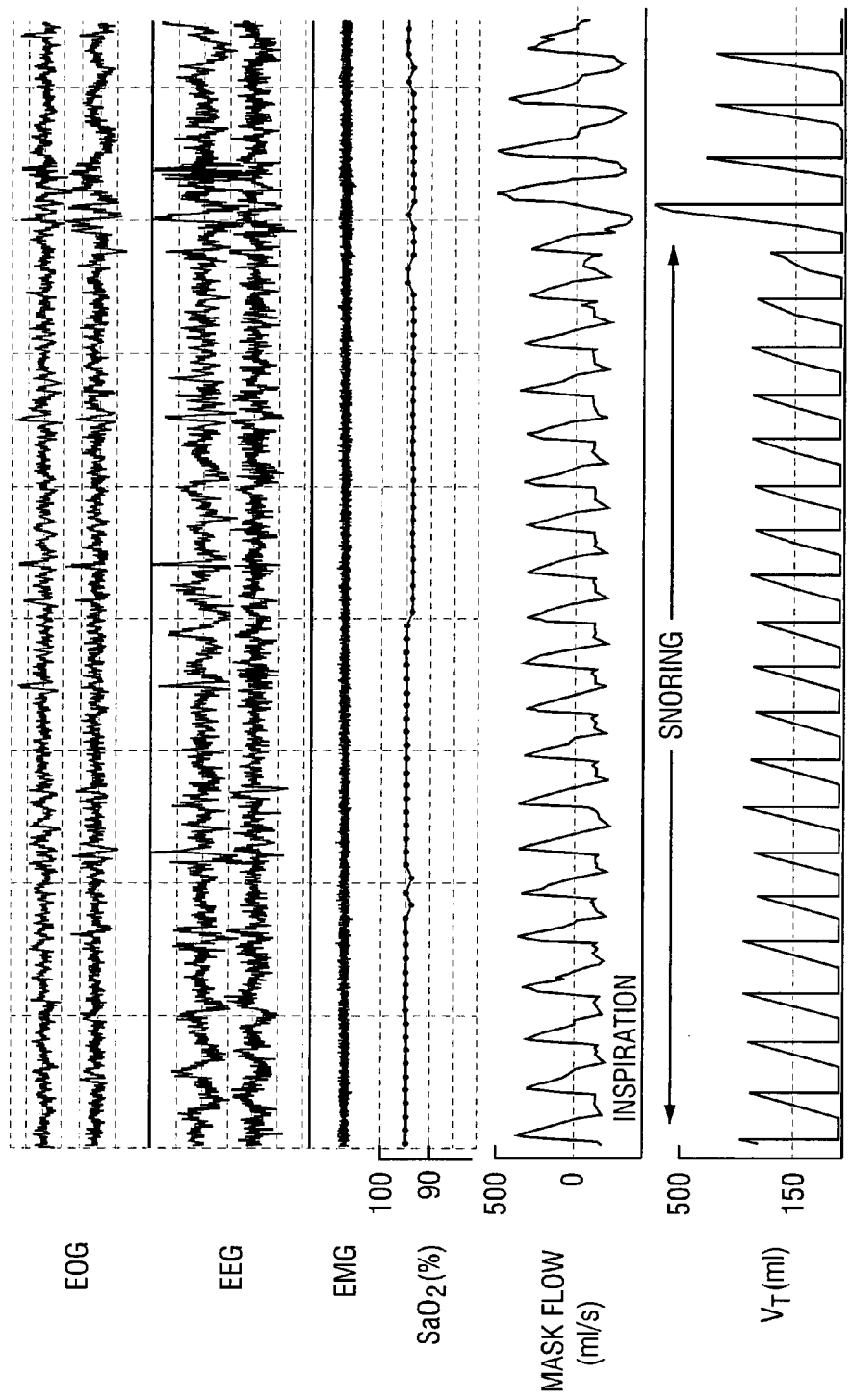
FIG. 9 is a graph of a snoring pattern.

FIG. 9 shows a sample trace of data obtained for a subject with snoring. The inspiratory tidal volume (VT) during a brief period of snoring indicates inadequate ventilation at the end of the snoring period. FIG. 9 shows the following parameters: EOG: Electrooculogram, EEG: Electroencephalogram: $SaO_2$, oxygen saturation: and VT: Tidal inspiratory volumes, as determined with the prototype monitor.

The snoring pattern in FIG. 9 is associated with no significant changes in the oxygen saturation ($SaO_2$) or the peak inspiratory flow. These two indicators have historically been relied upon for diagnosis of adequate ventilation, and they would both suggest in this case that the patient is getting adequate ventilation during the snoring period. However, the flow sensor measures ventilation and allows the clinician to observe that tidal volumes ($V_T$) significantly decreased during this period. As shown in FIG. 9, the tidal inspiratory volumes at the end of a snoring period reduces tidal volume substantially (e.g., tidal inspiratory volumes are less than 200 ml, which is slightly above the anatomic dead space of the upper airway). In other words, although there is significant air flow throughout the snoring period, tidal volume declines to levels such that almost all of the inspiratory air is entering the anatomic dead space (upper airways) but no longer entering the lungs. In summary, this example illustrates that the measurement of tidal volume allows the physician to determine the degree of upper airway obstruction and ventilation not yet possible with current semi-quantitative measurements of air flow.

Flow measurement in the range 0 Lpm to 200 Lpm compares to the pneumotachograph to within 5 Lpm. Special consideration can be given to the low flow regime (less than 20 Lpm) that is critically important for diagnosing sleep disorders such as hypopnea and hypoventilation. Dead space volume of the sensor is less than 3 ml and the nose mask is less than 15 milliliters, both of which maintains patient comfort and minimize re-breathing of exhalation. A frequency response of up to 100 Hz is used to ensure that snoring can be detected. A flow resistance of less than 1.0 cm $H_2O/l/sec$ @ 200 l/min maintains patient comfort.

Figure 10:
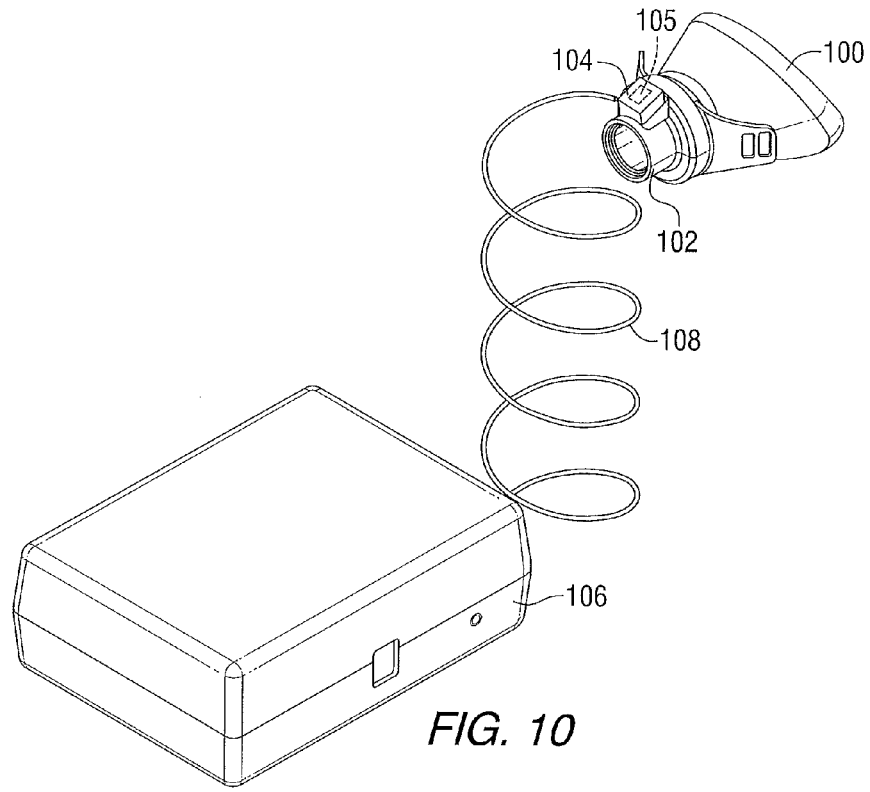
FIG. 10 is a pictorial representation of another embodiment of the invention.

FIG. 10 shows a pictorial representation of another embodiment of the breathing monitor. As shown in FIG. 10, the flow sensor is similar to the previously described embodiment including a mask 100 and a sensor body 102. In this embodiment, a small compartment 104 is added to house the electronics. The sensor body can be injection molded. This embodiment has the goal of minimizing the weight of the flow sensor, since the light weight is one of the major benefits of the flow sensor, and removing the cumbersome tubes. In this embodiment, the electronics are located adjacent to the flow sensor and all other components have been left in the tabletop module 106, which is connected to the electronics by a thin wire 108, to minimize the weight of the flow sensor. The electronics module can include an inclinometer 105 for measuring head position.

The inline meter shown in FIGS. 5a, 5b and 5c could also be equipped with on-board electronics similar to the mask flow sensor. For example, an electronics module could be mounted on the sensor body where tubes 44 and 46 exit the body.

Figure 11:
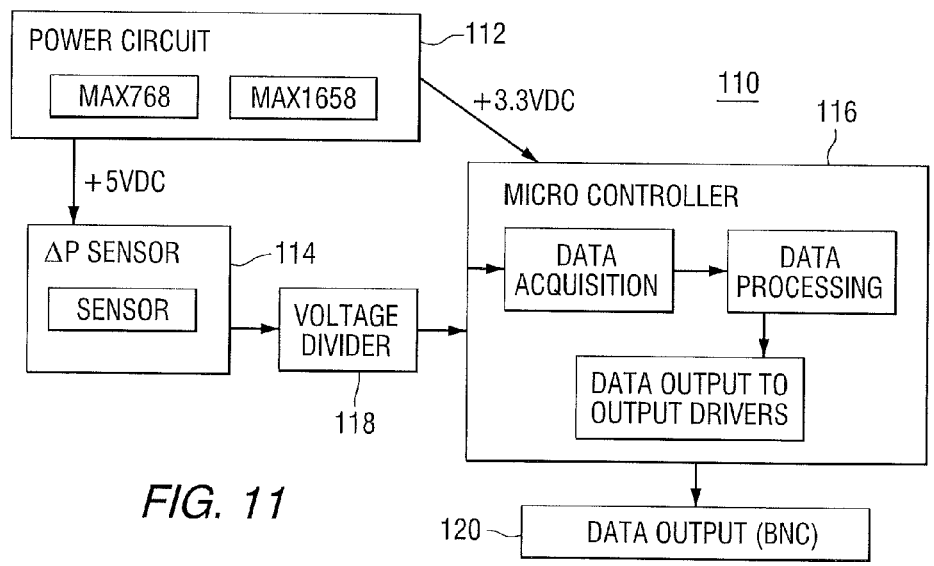
FIG. 11 is a block diagram of the monitor electronics.

FIG. 11 shows a block diagram of the electronics 110. The wire attaching the flow sensor to the tabletop electronics module can provide power to the sensor electronics and carry the sensor output back to the tabletop. The electronics includes several subsystems: a power subsystem 112, a sensor subsystem 114, and a data processing subsystem 116. Each subsystem can be constructed using commercially available electronics whereby the electrodes and probes reside at the mask. Two embodiments have been designed, one in which the power supply also resides within the apparatus, and another that places the power module externally in a tabletop unit. Which embodiment will be used depends on the diagnostic test (air flow alone or multiple channels) and the length of the recording. For example, in one embodiment, the power subsystem includes a 3.3 VDC voltage regulator and a +5 VDC voltage pump. The power subsystem provides a stable power source for the data processor and sensor subsystems. Voltage ripple from the +5 VDC must be less than 0.2 percent or 0.01 volts. All voltage regulation can be achieved using Maxim MAX1658 and MAX768 voltage regulators. Power to this system can be 6-12 VDC supplied by either a wall transformer or batteries.

Figure 12:
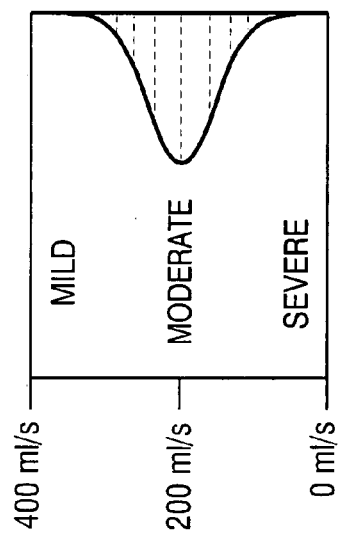
FIG. 12 is a graph showing an airway obstruction.
Figure 13:
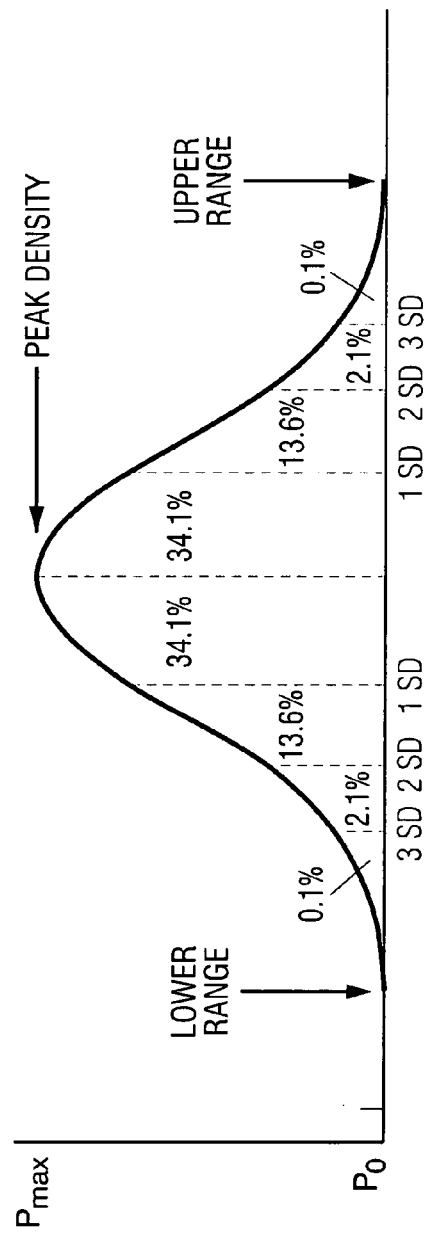
FIG. 13 is a graph of the probability density function of peak inspiratory air flow.

FIGS. 12 and 13 show the range of airway obstruction (represented by the spread or of the probability density function) and the predominant severity of airway obstruction (represented by the peak value of the probability density function). FIG. 12 shows an estimate of the level of airway obstruction and FIG. 13 shows the probability density function of peak inspiratory air flow for air flow limited breaths. This information can be displayed to provide feedback for therapeutic intervention and decision making for therapists. This also provides the treating medical personnel with a mechanism to monitor air flow obstruction over time and compare changes with pharmacologic and surgical interventions.

Figure 14:
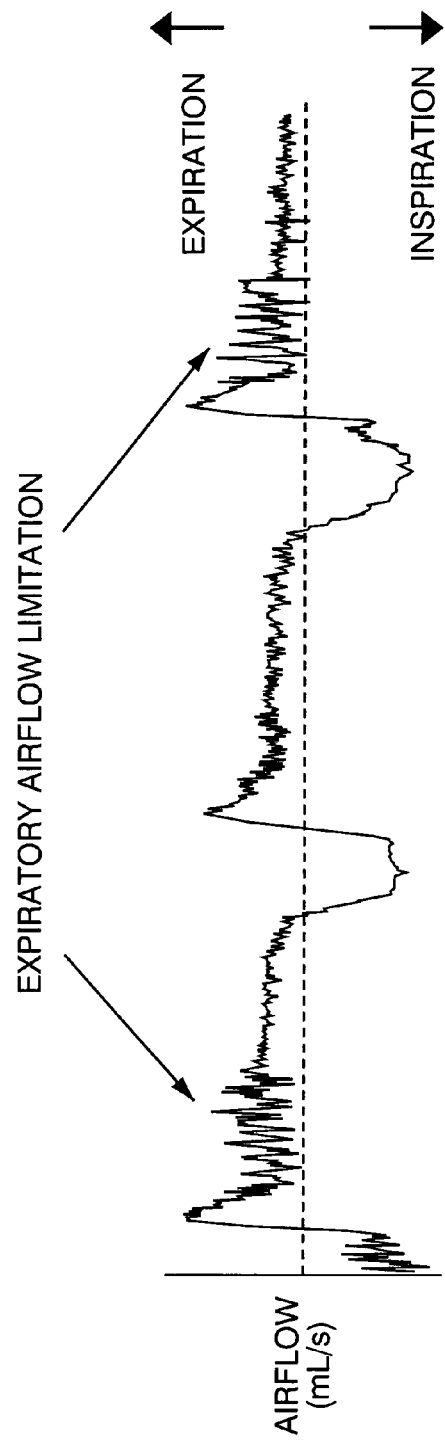
FIG. 14 is a graph of expiratory air flow obstruction.

FIG. 14 shows an example of an expiratory air flow limitation as measured by the invention.

The sensor subsystem includes a MEMs-based differential pressure sensor that uses an on-board ASIC to collect pressure readings from a MEMS diaphragm, providing a stable temperature compensated reading. The pressure sensor can be, for example, a Silicon Microstructures SM5812 differential pressure sensor, although, several alternatives to that sensor are commercially available.

The data processing system is responsible for acquiring sensor data, processing acquired data and reporting results in several different output formats. In one embodiment, all data processing is performed using a Cygnal C8051F000 8051 based mixed signal microcontroller. Improved precision can be provided by using at least a 16-bit A/D converter (ADC).

The data acquisition system is responsible for taking high speed data samples from the pressure sensor. The data acquisition system includes a voltage divider 118 that feeds the divided input voltage from the sensor into an analog-to-digital converter (ADC) internal to the microcontroller. The input of the ADC is polled at a rate of 50 kHz for short periods of time in order to obtain a maximum number of measurements possible in the shortest period of time. This allows for a high degree of signal averaging, (yielding an effective 16-bits of ADC resolution from a 12-bit ADC core in the case of the prototype electronics).

The data processing subsystem applies mathematical models to the differential pressure information supplied by the data acquisition subsystem and converts the differential reading into a flow rate. The input to this system is the digital data supplied by the data acquisition subsystem. The output from this system is the calculated air flow measurement.

A data reporting/posting system is responsible for taking input data from the data processing subsystem and making this information available to the end-user. A 0-5 V DC output voltage signal proportional to the measured air flow is provided. This signal can travel through the wire connecting the flow sensor to the tabletop module, and can be available to the user at the BNC jack 120 on the tabletop module.

Tables 1-4 compare state of the art pneumotachographs and nasal masks with the invention. Table 1 shows several parameters for available pneumotachographs. Table 2 shows the same parameters for devices made in accordance with this invention. Table 3 shows several parameters for available CPAP systems. Table 4 shows the same parameters for devices made in accordance with this invention.

TABLE 1

State of the Art Pneumotachographs

| Pneumotachograph | Flow Range | Weight | $V_D$ |
|---|---|---|---|
| #1 | (0-160 L/min) | 50.3 g | 14 ml |
| #2 | (0-400 L/min) |  | 51 ml |
| #3 | (0-800 L/min) | 243.5 g | 88 ml |

TABLE 2

Invention

|  | Flow Range | Weight | $V_D$ |
|---|---|---|---|
| Model A (in-mask) | (0-800 L/min) | 3.7 g | 2.8 ml |
| Model B (inline) | (0-800 L/min) | 6.6 g | 15 ml |

TABLE 3

Conventional CPAP Masks and Headgear

| CPAP |  | Weight | $V_D$ |
|---|---|---|---|
| #1 | Mask | 80.8 g | 90 ml |
|  | Headgear | 27.5 g |  |
| #2 | Mask | 103.0 g | 105 ml |
|  | Mask | 28.4 g |  |

TABLE 4

Invention

|  | Weight | $V_D$ |
|---|---|---|
| Mask | 12 g | <10 ml |
| Headgear | 3.3 g |  |

As can be seen, the invention substantially reduced dead space (VD) and weight.

The sleep and breathing monitor of this invention could be used in several settings/applications, including as a portable breathing monitor for use in inpatient and outpatient units, intensive care units, in post surgery transitional care units, and in pediatric units for monitoring ventilation in patients with neural disorders or heart and lung diseases and infants at risk for breathing disturbances or SIDS. The invention can also be used as a sleep apnea monitor. In conjunction with automated signal processing, the sleep and breathing monitor may become a screening tool for early detection of sleep apnea, Cheyne Stokes Respiration in patients with heart failure or pulmonary and neurological diseases.

The invention can also be used as an alveolar hypoventilation monitor. Alveor hypoventilation predisposes to respiratory failure. Contributing factors are morbid obesity and neuromuscular disturbances particular during sleep. Currently, there is no device that accurately allows the determination of the level alveolar ventilation.

The invention can provide respiration flow measurement in the range 0 Lpm to 200 Lpm and has an accuracy comparable to the pneumotachograph. Wider or narrower flow ranges can be obtained by selecting different commercially available pressure sensors. The MEMs sensors are particularly accurate in the low flow regime (less than 20 Lpm) that is critically important for diagnosing sleep disorders such as hypopnea and hypoventilation. The dead space volume is less than 20 milliliters to maintain patient comfort and minimize re-breathing of exhalation. A frequency response of up to 100 Hz is provided to ensure that snoring can be detected. A flow resistance of less than 1.0 cm $H_2O/L/sec$ @ 200 L/min maintains patient comfort. In addition to the above performance criteria, estimated production level manufacturing costs are sufficiently low to support a single use disposable flow metering section. A display (item 61 in FIG. 3) unit shows continuous, stable air flow signal throughout an entire sleep study.

The invention can be used to classify subtle respiratory events during sleep, such as hypopneas and hypoventilation, not yet possible with standard PSG (pulse-oximeter, respiratory effort, EEG) sensors due to inaccuracies of nasal cannulas and thermistors. A snap-together interface for the electronics module and the flow sensor can be used to improve cleanibility and make the flow sensor disposable. Inclusion of a nose or forehead mounted pulse oximeter which, coupled with the flow measurement, can make an improved package for monitoring ventilation, especially in ambulatory applications.

Moreover, the invention allows detection of expiratory airway obstruction. Thus, overnight sleep studies in patients with chronic obstructive pulmonary disease (COPD) and asthma with known degrees of upper airway obstruction and expiratory flow limitation can be used to demonstrate the ability to determine degrees of upper airway obstruction and expiratory flow limitation from a continuous air flow signal, not yet possible with standard PSG sensors.

The breathing monitor permits a "Plug and Play" use, without performing laborious calibration procedures. The sensors for measuring ventilation and sleep can be integrated into the mask and headgear for making measurements easily applicable even for non-specialized health care providers. The disposable unit allows for single use of the flow monitor to prevent transmission of communicable diseases. The single use of the breathing monitor makes it unnecessary to sterilize the device prior to each measurement. The invention is compact compared to the bulky state of the art polysomnographic monitor systems, which extends the range of applicability in areas not yet possible, e.g., in infants with smaller airways or in adults too sick to be transferred to specialized centers.

This invention solves four problems associated with state of the art polysomnography while providing a comparable accuracy. First, in one embodiment, the flow sensor unit includes a MEM (Micro Electro-Mechanical) pressure transducers, which are highly sensitive and stable once they have been pre-calibrated. This stability makes time-consuming calibration procedures unnecessary prior to each measurement and provides accurate measurements over time. Thus, the air flow monitor guarantees an accurate measurement of ventilation for individuals and patients, and is particularly suited for detecting sleep related breathing disorders.

Second, the electrical sensors can be integrated in the mask and headgear and thereby allow a fast and easy "hook up" of all sensors and allow measuring standard polysomnographic parameters such as oxygen saturation, snoring, EEG, EOG and body position, and movements. Thus, the design of all sensors would obviate the "hook up" of sensors by highly trained sleep technicians while guaranteeing a similar setup of measured signals for assessing sleep disordered breathing. The monitor, therefore, would allow an easy way for measuring sleep and breathing both in the sleep laboratory setting and outside conventional sleep laboratories.

Third, because the apparatus is designed for single use, the monitor system is a disposable and a far cheaper way to prevent transmission of infectious material between patients than is cleaning the currently used electrodes and sensors of standard polysomnographic monitor systems. Thus, the new breathing monitor guarantees a safe and accurate measurement of sleep disordered breathing for individuals and patients especially in areas to prevent communicable diseases.

Fourth, because of its low weight and low dead space, long term monitoring of ventilation is now possible. The current technology is too cumbersome for long term measurements as it disturbs breathing (through significant increases in dead space) and if worn during sleep, the sleep architecture. The present invention reduces the weight and dead space to insignificant levels. Thus long term measurements without altering ventilation and sleep are now possible. The flow sensor of this invention is light weight and comfortable during sleep, resulting in a high level of patient acceptance (both for adults and children) and can provide an accurate, quantitative air flow measurement, comparable to existing pneumotachographs.

The invention may be used for patients too ill or otherwise constrained from attending sleep clinics for care. PSG for such patients in other healthcare environments (nursing homes, hospitals) could be made more affordable and accessible with use of an accurate disposable flow sensor. Home diagnostic use is also possible.

The electronics unit can be re-used with no interim maintenance or calibration. To achieve comparable accuracy, the pneumotachograph and its metering section must be cleaned and recalibrated between patients. The capital cost, maintenance requirements and patient discomfort limit the use of the pneumotachograph to the sleep lab setting and seriously constrain consideration of its use for a portable system.

The differential pressure is measured at the center of the sensor body air passage. This is superior to other measurement positions because it is less susceptible to measurement errors due to fouling of the ports. A previously described flow sensor had a series of ports positioned across the flow stream that effectively average the differential pressure signal, theoretically reducing susceptibility to noise due to turbulence. If one port gets partially or fully clogged, the differential pressure measurement will be biased towards the remaining open ports. The flow sensor of this invention is not susceptible to this potential problem.

The invention provides a quantitative measurement of ventilation and the severity of upper airway obstruction for use in clinical sleep studies, in ambulatory settings, and eventually as a home diagnostic system. The development of an accurate, comfortable flow sensor for sleep applications can facilitate high throughput clinical and physiological studies that can expand the knowledge in both clinical and translational research. The flow sensor can have an immediate impact on patient monitoring in sleep laboratories and in pulmonary medicine and anesthesia. The flow sensor can form the cornerstone of a home diagnostic system that can greatly increase the diagnosis of sleep disorders. The flow sensor is well suited for this application because it is easy to use, comfortable, and provides a quantitative measure of air flow that, coupled with a pulse oximeter, can comprise a complete home diagnostic system.

There is a need for a flow sensor that is both accurate and comfortable to wear during sleep. This invention is critically important for filling this need in the field of adult and pediatric sleep medicine. The invention can also be used in other applications. For example, the invention can be used as a monitoring and screening device for subjects susceptible to disturbed breathing. This is particularly important in medical areas such as anesthesia, critical care units and medical areas dealing with disorders that affect the cardiopulmonary system and gas exchange.

While the invention has been described in terms of several embodiments, it can be apparent to those skilled in the art that various changes can be made to the described embodiments without departing from the scope of the invention as set forth in the following claims.

What is claimed is:

1. An apparatus comprising:
    a mask;
    a sensor body configured to be attached to the mask and to provide a substantially unobstructed breathing passage therethrough for a user, wherein said sensor body comprises an airflow sensor defining first and second air passages with corresponding first and second ports for sampling corresponding first and second air pressures, said airflow sensor being arranged with said first and second ports facing opposite directions substantially along a path of airflow through said sensor body;
    a plurality of straps directly connected to the sensor body for securing the sensor body and mask to said user, wherein the straps are configured to place a force on the sensor body to maintain an appropriate fit between the mask and said airflow sensor within the sensor body; and
    an electronic module comprising a differential pressure sensor operatively connected to said airflow sensor to provide electrical signals corresponding to said first and second air pressures detected in corresponding said first and second air passages of said airflow sensor,
    wherein the electronic module is further configured to process said electrical signals corresponding to said first and second air pressures to determine a velocity of airflow through said sensor body based on a difference between said first and second air pressures and areas of said first and second ports, and
    wherein the sensor body has a flow resistance of less than 1.0 cm/$H_2O$/L/sec at 200 L/min.

2. The apparatus of claim 1, wherein the sensor body includes an annular opening, and the mask includes a ring, wherein the ring forms a press fit in the annular opening.

3. The apparatus of claim 2, wherein the ring includes at least one groove and the annular opening includes at least one ridge configured to fit within the at least one groove.

4. The apparatus of claim 1, wherein the electronic module includes: a micro-electromechanical sensor.

5. The apparatus of claim 1, further comprising:
    an oximeter mounted in the mask.

6. The apparatus of claim 1, wherein the electronic module is mounted on the sensor body.

7. The apparatus of claim 1, further comprising at least one additional sensor for monitoring at least one of: oxygen saturation, muscle activity, brain wave activity, eye movement, head position, head movement, and/or heart rate.

8. The apparatus of claim 1, further comprising:
    a display for patient feedback.

9. The apparatus of claim 1, wherein the mask covers only a nose.

10. The apparatus of claim 1, wherein the mask covers a nose and mouth.

11. The apparatus of claim 1, wherein the mask is made of molded rubber of silicone.

12. The apparatus of claim 1, further comprising:
    an inclinometer positioned on the sensor body for measuring head orientation.

13. The apparatus of claim 12, wherein the inclinometer is integrated directly into the electronic module.

14. The apparatus of claim 1, wherein a differential pressure measurement is made at a center of a flow stream.

15. The apparatus of claim 1, wherein the electronic module is mounted on the sensor body.

16. The apparatus of claim 1, wherein the electronic module transmits signals to a base unit wirelessly.

17. The apparatus of claim 1, wherein the mask has a dead space of less than 15 ml.

18. The apparatus of claim 1, wherein the electronic module has a frequency response of up to 100 Hz.

19. A device for at least one of measuring and monitoring breathing airflow of a user, comprising:
    a sensor body defining a substantially unobstructed breathing passage for said user therethrough, the sensor body comprising an airflow sensor defining first and second air passages with corresponding first and second ports for sampling corresponding first and second air pressures, said airflow sensor being arranged with said first and second ports facing opposite directions substantially along a path of airflow through said sensor body; and
    an electronic module comprising a differential pressure sensor operatively connected to said airflow sensor to provide electrical signals corresponding to said first and second air pressures detected in corresponding said first and second air passages of said airflow sensor,
    wherein said electronic module is further configured to process said electrical signals corresponding to said first and second air pressures to determine a velocity of airflow through said sensor body based on a difference between said first and second air pressures and areas of said first and second ports, and
    wherein the sensor body has a flow resistance of less than 1.0 cm/$H_2O$/L/sec at 200 L/min.

20. The device according to claim 19, wherein said differential pressure sensor is a micro electromechanical systems (MEMS) sensor.

21. The device according to claim 20, wherein said sensor body and said electronic module are packaged together in a single unit free of external components connected by wires or tubes.

22. The device according to claim 19, wherein said sensor body is configured to be attached to at least one of a mask or a breathing tube for a breathing device.

23. The device according to claim 19, wherein said sensor body has a dead space of less than 15 milliliters.

24. The device according to claim 19, wherein said sensor body has a dead space of less than 10 milliliters.

25. The device according to claim 19, wherein said sensor body has a dead space of about 3 milliliters.

26. The apparatus of claim 19, wherein said electronic module comprises a wireless transmitter.

* * * * *